(12) United States Patent
Outred et al.

(10) Patent No.: US 7,806,844 B2
(45) Date of Patent: Oct. 5, 2010

(54) PLANTAR-FLEXION RESTRAINT DEVICE

(75) Inventors: Kevin Outred, Kingsley (AU); Matthew Symington, Eltham (AU)

(73) Assignee: United Pacific Industries Pty Ltd., Kilsyth (AU)

( * ) Notice: Subject to any disclaimer, the term of this patent is extended or adjusted under 35 U.S.C. 154(b) by 129 days.

(21) Appl. No.: 11/658,497

(22) PCT Filed: Jul. 28, 2005

(86) PCT No.: PCT/AU2005/001108

§ 371 (c)(1),
(2), (4) Date: May 11, 2007

(87) PCT Pub. No.: WO2006/010213

PCT Pub. Date: Feb. 2, 2006

(65) Prior Publication Data

US 2008/0004558 A1    Jan. 3, 2008

(30) Foreign Application Priority Data

Jul. 29, 2004   (AU) .............................. 2004904261

(51) Int. Cl.
*A61F 13/00* (2006.01)
*A61F 5/00* (2006.01)

(52) U.S. Cl. ................. 602/28; 602/5; 602/60

(58) Field of Classification Search ............ 602/27–29, 602/60–66, 5; 128/869, 882; 2/239, 240; 601/27

See application file for complete search history.

(56) References Cited

U.S. PATENT DOCUMENTS

| | | | |
|---|---|---|---|
| 2,557,603 A | 6/1951 | Invidiato | |
| 3,334,356 A * | 8/1967 | Abel | 2/239 |
| 3,827,430 A | 8/1974 | Fadden | |
| 3,916,886 A | 11/1975 | Rogers | |
| 3,976,059 A | 8/1976 | Lonardo | |
| 4,294,238 A | 10/1981 | Woodford | |
| 4,329,982 A | 5/1982 | Heaney | |
| 4,497,070 A | 2/1985 | Cho | |
| 4,559,934 A * | 12/1985 | Philipp | 602/27 |
| 4,562,834 A * | 1/1986 | Bates et al. | 602/3 |
| 4,566,447 A * | 1/1986 | Deis | 602/28 |
| 4,998,722 A * | 3/1991 | Scott | 482/79 |
| 5,020,523 A | 6/1991 | Bodine | |
| 5,088,480 A | 2/1992 | Wang | |
| 5,176,623 A | 1/1993 | Stetman et al. | |
| 5,197,942 A | 3/1993 | Brady | |
| 5,298,013 A | 3/1994 | Lonardo | |
| 5,382,224 A | 1/1995 | Spangler | |
| 5,399,155 A * | 3/1995 | Strassburg et al. | 602/28 |

(Continued)

FOREIGN PATENT DOCUMENTS

DE    8700823    3/1987

(Continued)

*Primary Examiner*—Kim M Lewis
(74) *Attorney, Agent, or Firm*—Kenyon & Kenyon LLP

(57) ABSTRACT

A device for a subject having plantar fasciitis, the device comprising: (a) an elastic sock (10), (b) a leg binding (15) and (c) an elastic strap (20), wherein in use the elastic strap extends from adjacent a toe portion of the elastic sock to the leg binding so as to restrain the plantar fascia from flexion, yet permits the subject to walk and exercise the plantar fascia.

31 Claims, 7 Drawing Sheets

U.S. PATENT DOCUMENTS

| | | | |
|---|---|---|---|
| 5,431,624 A | 7/1995 | Saxton et al. | |
| 5,472,414 A * | 12/1995 | Detty | 602/27 |
| 5,486,157 A | 1/1996 | DiBenedetto | |
| 5,605,535 A | 2/1997 | Lepage | |
| 5,843,010 A | 12/1998 | Bodmer | |
| 6,695,797 B2 | 2/2004 | Trieloff | |
| 2004/0043879 A1 | 3/2004 | Huang | |

FOREIGN PATENT DOCUMENTS

| | | |
|---|---|---|
| DE | 9000985 | 7/1990 |
| DE | 3925530 A1 * | 2/1991 |
| FR | 2586907 | 3/1987 |
| JP | 2001098401 A * | 4/2001 |
| WO | 02098333 | 12/2002 |

\* cited by examiner

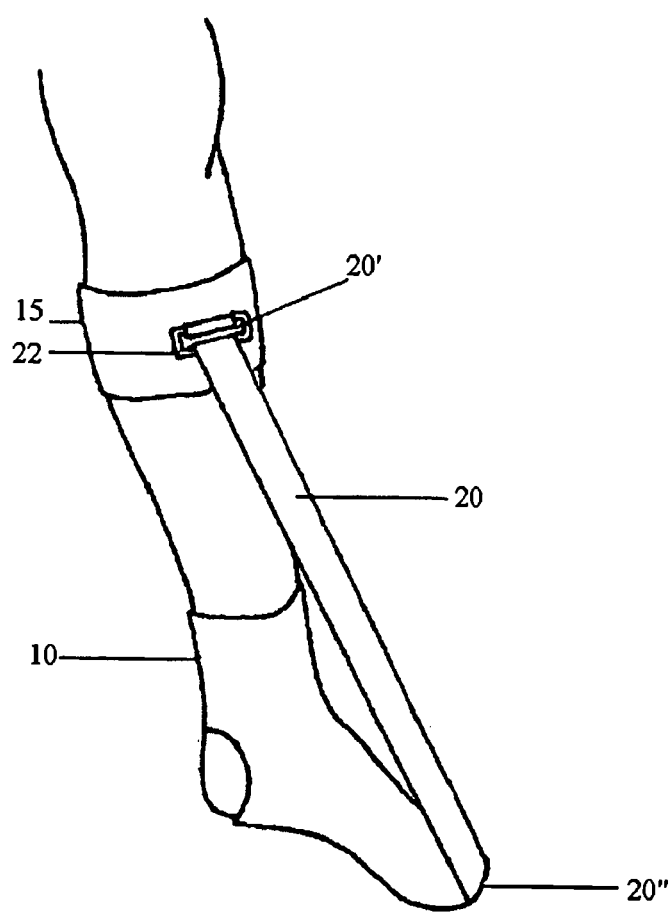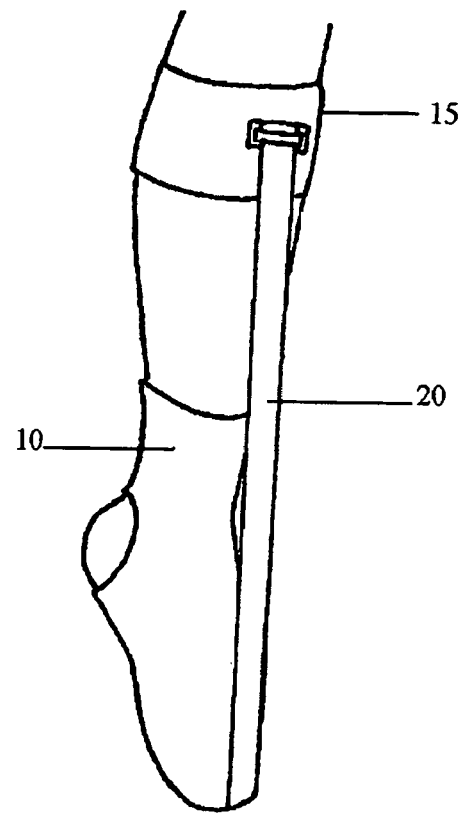
FIGURE 2A
FIGURE 2B

PLANTAR-FLEXION RESTRAINT DEVICE

This is a 371 national phase application of PCT/AU2005/001108 filed 28 Jul. 2005, which claims priority to Australian Patent Application No. 2004904261 filed 29 Jul. 2004, the contents of which are incorporated herein by reference.

FIELD OF THE INVENTION

The present invention relates to a device for restraining plantar flexion. In particular it relates to a device for restraining plantar flexion in a person having inflammation or other disorder of the plantar fascia. More particularly the present invention relates to a restraint device for restraining contraction of the plantar fascia, preferably keeping the plantar fascia in a neutral to slight dorsiflexion by passive static tension.

BACKGROUND OF THE INVENTION

In this specification where a document, act or item of knowledge is referred to or discussed, this reference or discussion is not an admission that the document, act or item of knowledge or any combination thereof was at the priority date, publicly available, known to the public, part of the common general knowledge or known to be relevant to an attempt to solve a problem with which this specification is concerned.

While the present invention will be described with particular reference to the disorder known as 'heel spur' the invention is not so limited but relates more generally to disorders or inflammation of the plantar fascia.

The plantar fascia (also known as the plantar aponeurosis) is a thick fibrous material that covers the soft tissue on the sole of the foot, providing static support for the medial longitudinal arch of the foot. The plantar fascia originates at the heel (specifically, at the medial tuberosity of the calcaneus), spreads out over the sole of the foot and terminates in the ligaments near the teratarsal heads in the forefoot. In use it helps to restrain motion within the joints of the ankle and forefoot.

The plantar fascia can become inflamed as a result of stress caused by overuse or as a result of a condition such as heel spur. Heel spurs typically develop as an abnormal growth in the front and bottom of the heel bone due to calcium deposits that form when the plantar fascia pulls away from the heel. Initially, sufferers commonly experience a dull intermittent pain in the heel which may develop into a sharp persistent pain. But it is not the spur that causes pain. The pain is caused by inflammation of the plantar fascia (known as plantar fasciitis). The classic sign of plantar fasciitis is heel pain with the first few steps in the morning. The pain is usually in the front and bottom of the heel, but it can be over any portion of the bottom of the foot where the plantar fascia is located. The pain varies in intensity from person to person and it can last a few months, become permanent, or come and go. Striking of the heel on the ground can exacerbate the condition, but is not a cause of the inflammation.

Causes of heel spur and subsequent inflammation of the plantar fascia include inadequate flexibility in the calf muscles, lack of arch support or sole cushioning in footwear, footwear that has inflexible soles, overweight, injury, sudden increase in physical activity, and spending too much time on the feet. Other causes of inflammation of the plantar fascia include arthritis, heel bone damage ("stress fracture"), loss of natural tissue for cushioning under the heel ("fat pad atrophy") and tarsal tunnel syndrome.

The key to proper treatment of plantar fasciitis is determination of what is causing the excessive stretching of the plantar fascia. However in many cases, finding a specific cause is difficult. Typically, plantar fasciitis is treated with the use of a mixture of approaches as appropriate to the sufferer. These include losing weight, the use of orthotics, increasing cushioning in the sole of shoes, resting the foot, applying supporting tape and wearing of night splints. Application of ice often helps to reduce pain although many sufferers find it necessary to use analgesics such as ibuprofen cream that can be applied directly to painful areas. In more severe cases injections of painkillers may be used. Stretching the calf muscles using exercises that do not re-injure the fascia is a cure for many people. Typically these exercises are performed 3 times a day and especially before getting out of bed in the morning. Surgery may be necessary in extreme cases of plantar fasciitis.

Orthotic based treatment for plantar fasciitis include elevating the heel with the use of a heel cradle or heel cup. Heel cradles and heel cups provide extra comfort and cushion to the heel, and reduce the amount of shock and shear forces experienced from everyday activities. When the cause of plantar fasciitis is over-pronation (flat feet), an orthotic with rearfoot posting and longitudinal arch support is an effective device to reduce the over-pronation, and allow the condition to heal.

Many different devices have been developed to treat plantar fasciitis, particularly plantar fasciitis caused by heel spur. One such device for treatment of plantar fascia is described in U.S. Pat. No. 5,399,155 (Strassburg et al) and consists of an over the calf sock having a reinforced adjustable support strap attached around the upper portion of the sock with a "D" ring attached to the front (shin) side. A reinforced inelastic adjustable strap is attached to the toe of the sock, with a hook and loop assembly attached for closure. When this strap is passed through the "D" ring and secured by means of the hook and loop assembly, the plantar fascia can be maintained in the desired position. One of the disadvantages of this type of device, and many other orthotic devices, is that they hold the foot quite rigid so the wearer cannot walk. The device of U.S. Pat. No. 5,399,155 has an inelastic support strap hindering the normal action of the foot and ankle during walking hence use of the device is limited to times when the wearer is asleep or resting. Furthermore, solely treating heel spur by holding the plantar fascia in a neutral position and preventing movement or exercise is unlikely to cure heel spur.

Accordingly there is a need for a device having wider applicability, which can be used when the wearer is mobile as well as when they are sleeping or resting.

SUMMARY OF THE INVENTION

The present invention provides a device for a subject having plantar fasciitis, the device comprising (1) an elastic sock, (2) a leg binding and (3) an elastic strap wherein in use the elastic strap extends from adjacent a toe portion of the elastic sock to the leg binding so as to restrain the plantar fascia from flexion, yet permits the subject to walk and exercise the plantar fascia.

Typically the elastic sock fits over the foot of the wearer in the manner of a gauntlet. It may extend over the ankle of the wearer. In addition it may extend further up the calf to the knee, thus enclosing part or all of the tibia and fibula. The foot may be entirely enclosed or alternatively the sock may include one or more openings. For example the elastic sock may leave the heel exposed. Preferably the sock is of a size that fits snugly around the wearer's foot, ankle and calf. Alternatively the sock may be adjustable around the foot, ankle or calf so that a snug fit can be achieved. For example, the elastic sock may include adjustable straps or tapes. Preferably the elastic sock includes fastening material such as the hook and loop fastener known as Velcro™.

Typically the elastic sock has an upper surface and a lower surface. In use the upper surface of the elastic sock lies adjacent the top of the foot and the lower surface is adjacent the sole of the foot. The upper and lower surfaces may be integral. For example the upper and lower surfaces may be sewn or adhered together to provide a gauntlet for the wearer's foot.

Typically at least the upper surface or the lower surface of the elastic sock is constructed of flexible material that does not unduly restrict movement of the wearer's foot or ankle when exercising and walking. The flexible material may for example comprise a polymeric material such as flexible rubberized material, polypropylene or polyurethane. The elastic sock may consist of layers of different material.

The upper surface and lower surface of the elastic sock may be of the same, or different material. In a preferred embodiment the upper surface is comprised of polymeric material such as flexible rubberized material, polypropylene or polyurethane while the lower surface comprises a non-slip material to assist traction and avoid slipping as the wearer walks. For example, the lower surface may comprise flexible material coated with synthetic rubber having a raised pattern to improve the non-slip characteristics of the coating.

The elastic nature of the sock has the advantage of stimulating blood flow to the wearer's calf and foot, in contrast to many of the devices of the prior art that hold the foot and calf rigid or under compression so that blood flow is restricted and the natural recuperative functions of the body are inhibited. Preferably the elastic sock has thermotherapeutic properties, that is, it keeps the enclosed tissue warm so that blood flow, and thus healing are stimulated.

The principal function of the leg binding is to provide an anchor point on the wearer's leg for one end of the elastic strap. The leg binding may be integral with the elastic sock or it may be separate from the elastic sock. The leg binding may be located adjacent any part of the wearer's leg such as the ankle, or intermediate the ankle and the knee.

In one embodiment the leg binding is integral with the elastic sock, attached to the elastic strap by stitching or the like.

In another embodiment the leg binding is not integral with the elastic sock but can be removably attached. For example the leg binding may comprises a strip of material that can be wrapped around the calf or ankle of the wearer, held closed by hook and loop material fastening such as Velcro™. The elastic strap can be attached to the leg binding by Velcro or by a buckle.

The leg binding may be of any convenient length and width. Preferably the leg binding can be adjusted to ensure a snug fit around the calf or ankle so that the device does not move or become displaced when the wearer moves.

The leg binding is typically constructed of flexible material that does not unduly restrict movement of the wearer's foot or ankle. The leg binding may comprise the same material as the elastic sock, or it may comprise different material.

The elastic strap may comprise elastic material along its entire length that allows stretching in a longitudinal direction. Alternatively it may comprise elastic material along part of its length. Typically the ends of the elastic strap are reinforced with stronger material for attachment to the elastic sock and leg binding.

The elastic strap in combination with the rest of the device resists contraction of the plantar fascia when the wearer is at rest, preferably keeping the plantar fascia in a neutral to slight dorsiflexion by passive static tension, yet allow movement of the foot relative to the calf and ankle so that the wearer can walk when they want to or perform exercises that assist reduction of inflammation of the plantar fascia. For example, the wearer may wish to carry out exercises that stretch the calf muscle but do not re-injure the plantar fascia.

In use the elastic strap extends from the region of the elastic sock adjacent the wearer's toe to the leg binding. The elastic strap may be attached to the upper surface or the lower surface, or both surfaces of the elastic sock. Typically one end of the strap is integral with the lower surface of the elastic sock. Preferably it is attached to the part of the lower surface which lies under the toes of the wearer or near the ball of the foot. The end of the strap it typically attached to the elastic sock by adhesive or stitching.

The other end of the elastic strap may be integral with the leg binding, but more typically, it is removably attached to the leg binding by hook and loop material fastening such as Velcro. In another embodiment, the other end of the elastic strap is removably attached to the leg binding by a buckle, or plastic loop. The end of the binding may include Velcro so that it can be passed through the plastic loop and fastened to itself using the Velcro.

Preferably the end of the elastic strap adjacent the leg binding is adjustable so the overall length of the elastic strap can be modified in order to maintain static tension on the plantar fascia.

DRAWINGS

The invention will now be further described with reference to the following non-limiting drawings:

FIGS. 2a and 2b show a further embodiment of a device according to the present invention depicted in two different foot positions;

Figure 1A:
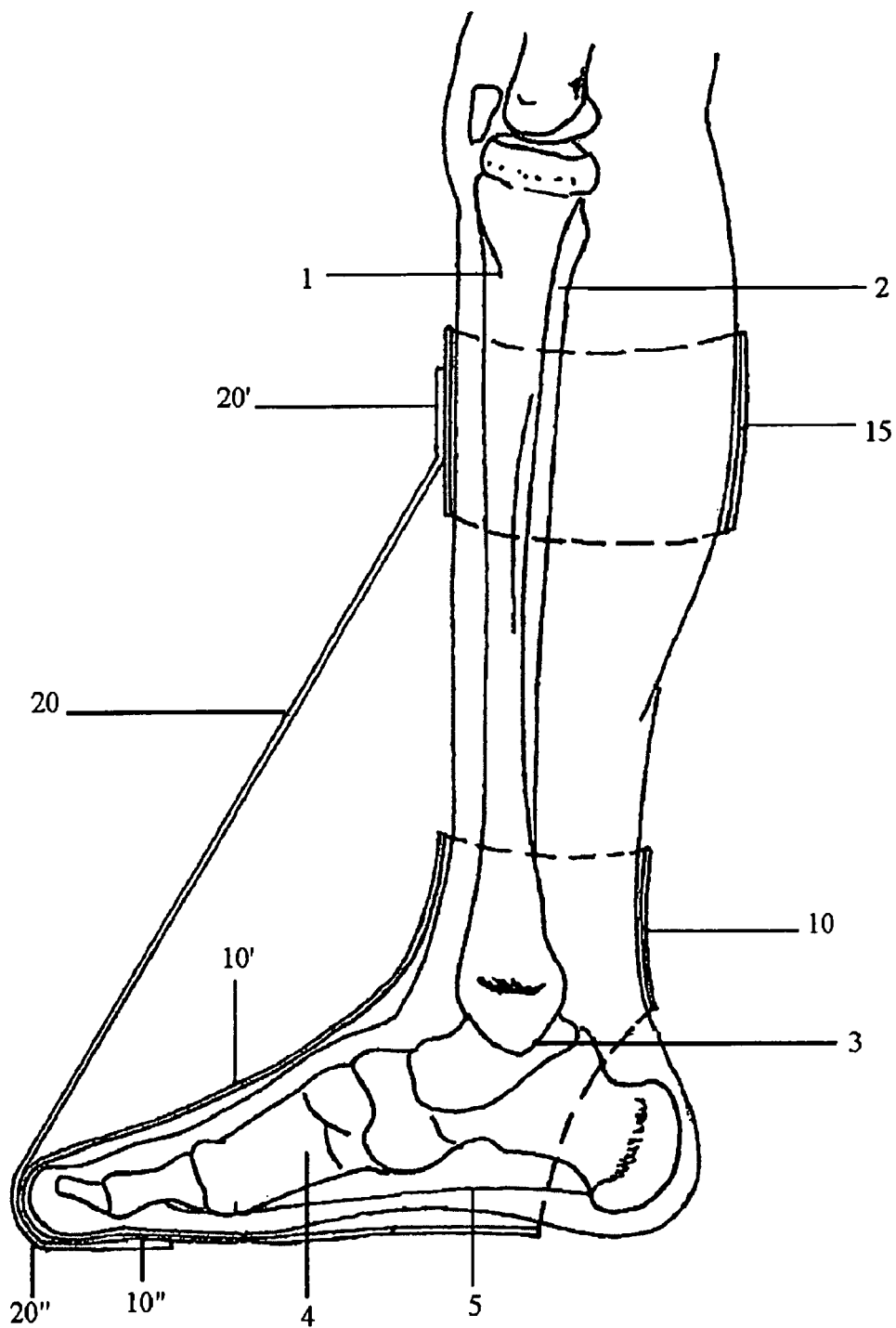
FIG. 1a shows a cross sectional view of a foot and ankle located in a device according to one embodiment of the present invention.

FIG. 1a shows a foot, ankle and calf located in a device (shown in cross section) according to one embodiment of the present invention. The foot is depicted in x-ray view to show the tibia (1), the fibula (2), the ankle (comprising the ends of the tibia and fibula, plus the talus underneath) (3), the foot bones (4) and the plantar fascia (5). The ankle joint is responsible for up and down motion of the foot.

In this view the foot is located within an elastic sock (10) that partially encloses the foot and ankle and encircles the lower part of the tibia and fibula, leaving the heel uncovered.

The elastic sock (10) has an upper surface (10') adjacent the top of the foot and a lower surface (10") adjacent the sole of the foot.

The leg binding (15) encircles the upper part of the tibia (1) and fibula (2). The elastic strap (20) is attached by Velcro at one end (20') to the leg binding (15) and attached by stitching at the other end (20") to the lower surface (10") of the elastic sock (10) near the ball of the foot.

Figure 1B:
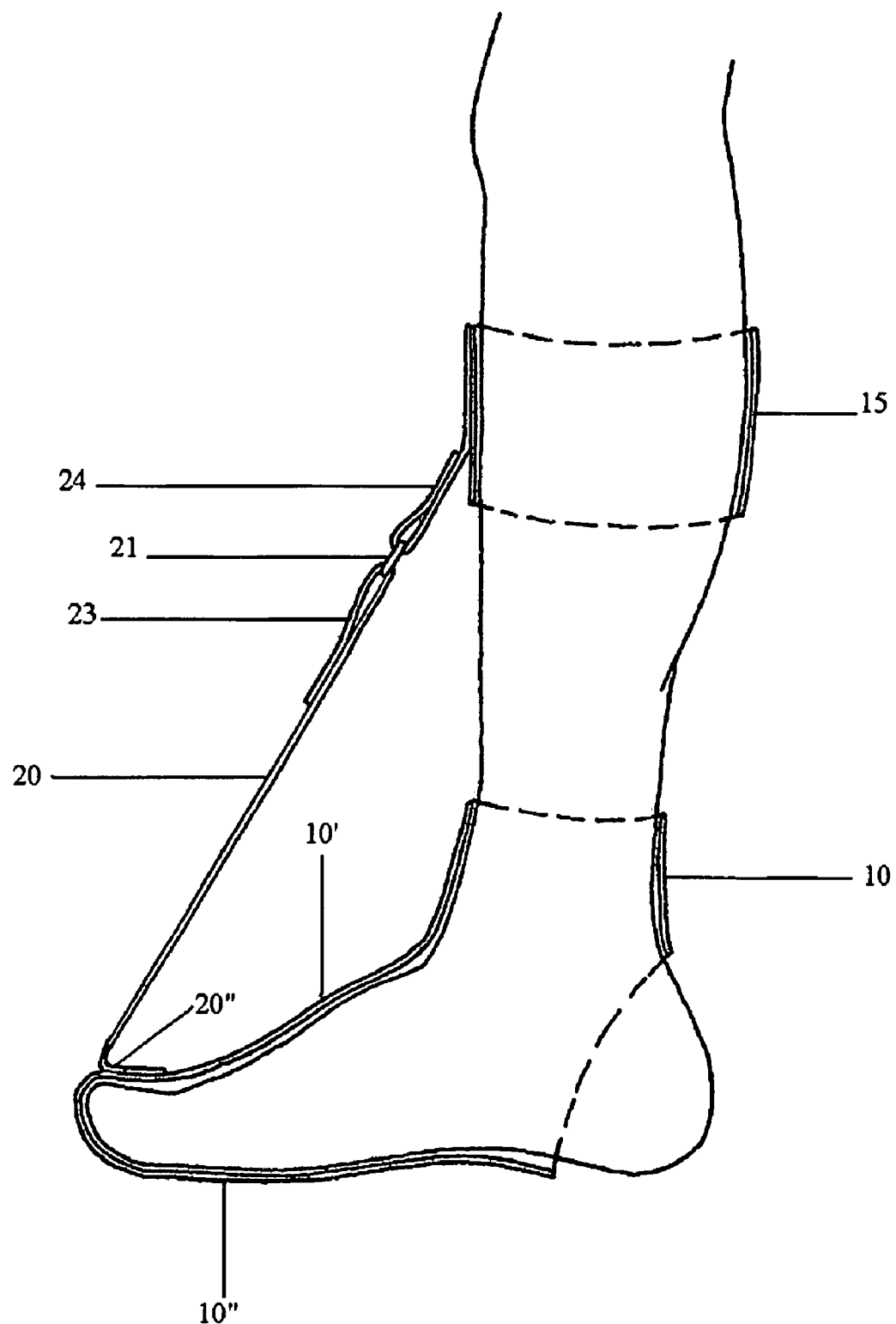
FIG. 1b shows a cross sectional view of a foot and ankle located in a device according to another embodiment of the present invention.

FIG. 1b shows a foot, ankle and calf located in a device (shown in cross section) according to a further embodiment of the present invention. In this view the foot is located within an elastic sock (10) having an upper surface (10') comprising a flexible polymeric material and a lower surface (10") comprising a flexible polymeric material having non-slip surface to improve the traction between the sole of the wearer's foot and the surfaces on which the wearer may walk.

The leg binding (15) encircles the upper part of the calf, just below the knee. The elastic strap (20) is attached at one end (20") by stitching to the upper surface (10') of the elastic sock (10) and at the other end to the leg binding (15). Intermediate the two ends of the strap is a plastic loop (21) which can be used to adjust the length of the elastic strap (20). Specifically the elastic strap (20) comprises two parts (23, 24), each of which has a free end. The free ends are passed through the plastic loop (21), and releasably secured back on themselves by Velcro™. The wearer can thus adjust the length of the elastic strap (20) and control the amount of passive static tension imposed on the plantar fascia.

FIG. 2 shows a further embodiment of the device of the present invention when in use, in two different positions. The device shown is similar to that shown in FIG. 1, except that the end (20') of the elastic strap (20) comprising Velcro is attached to the leg binding (15) by a plastic loop (22). The end (20') of the elastic strap is threaded through the loop (22) and fastened back on the elastic strap (20) by Velcro™ hook and loop fastening. This type of fastening provides a convenient means for adjusting the length of the elastic strap (20). FIG. 2 shows the leg of a subject wearing the device when their foot is flat on the ground (FIG. 2a) and when they stand on tiptoe (FIG. 2b). The elastic strap has sufficient stretch to maintain static tension on the plantar fascia when the foot is at rest, as well as allowing movement of the foot relative to the calf.

Figure 3:
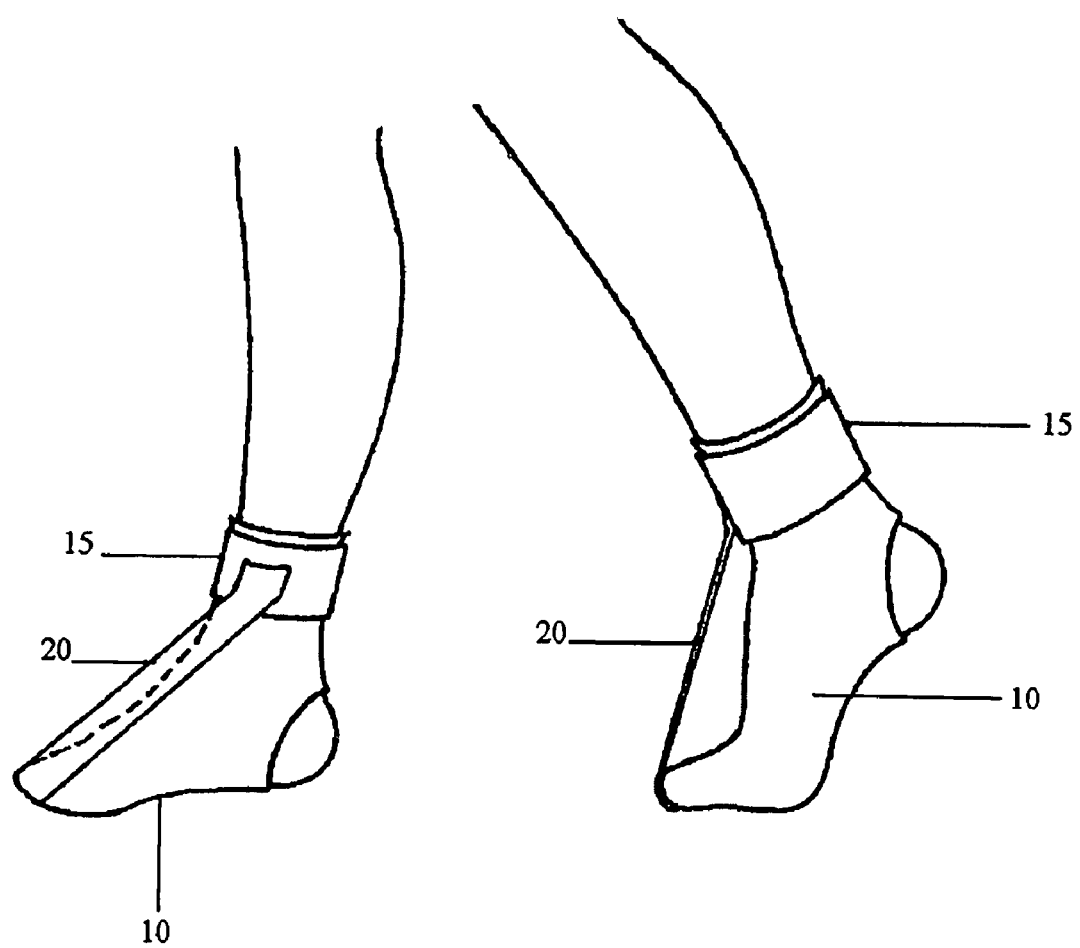
FIG. 3 shows a further embodiment of a device according to the present invention on a wearer who is walking.

FIG. 3 shows a further embodiment of the device according to the present invention on the left and right legs of a wearer who is walking. In this embodiment the leg binding (15) encircles the part of the elastic sock (10) that is located adjacent the ankle of the wearer.

Figure 4:
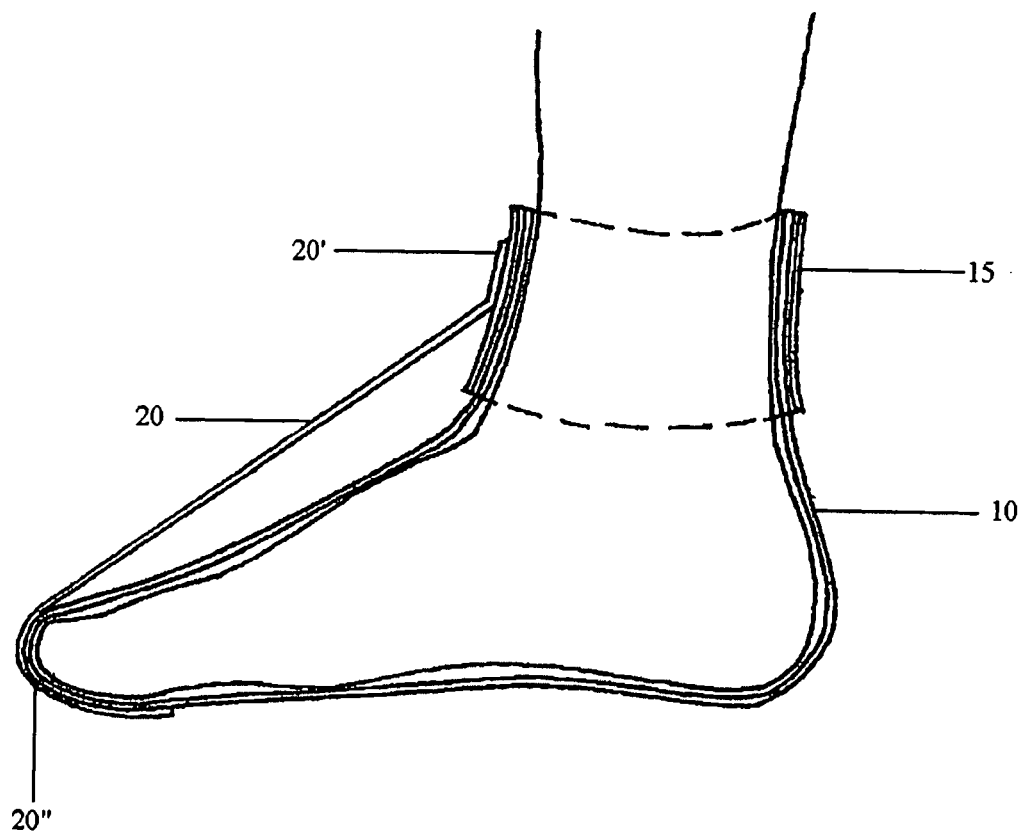
FIG. 4 shows a cross sectional view of a further device according to the present invention.

FIG. 4 shows a plan view of a further embodiment of the device of the present invention. In this embodiment the device is the same as that shown in FIG. 3 except that the heel is enclosed. The elastic sock (10) is an appropriate size for the wearer and in this embodiment the fit is non-adjustable. The sock is sufficiently elastic that it fits snugly to the form of the foot. The leg binding (15) is a strip of elastic material that snugly encircles the wearer's ankle or lower calf region and the ends of the strip are attached together by Velcro™. The elastic strap (20) is attached at one end (20") to the lower portion of the elastic sock, and at the other end (20') to the part of the leg binding (15) adjacent the front of the wearer's shin.

Figure 5:
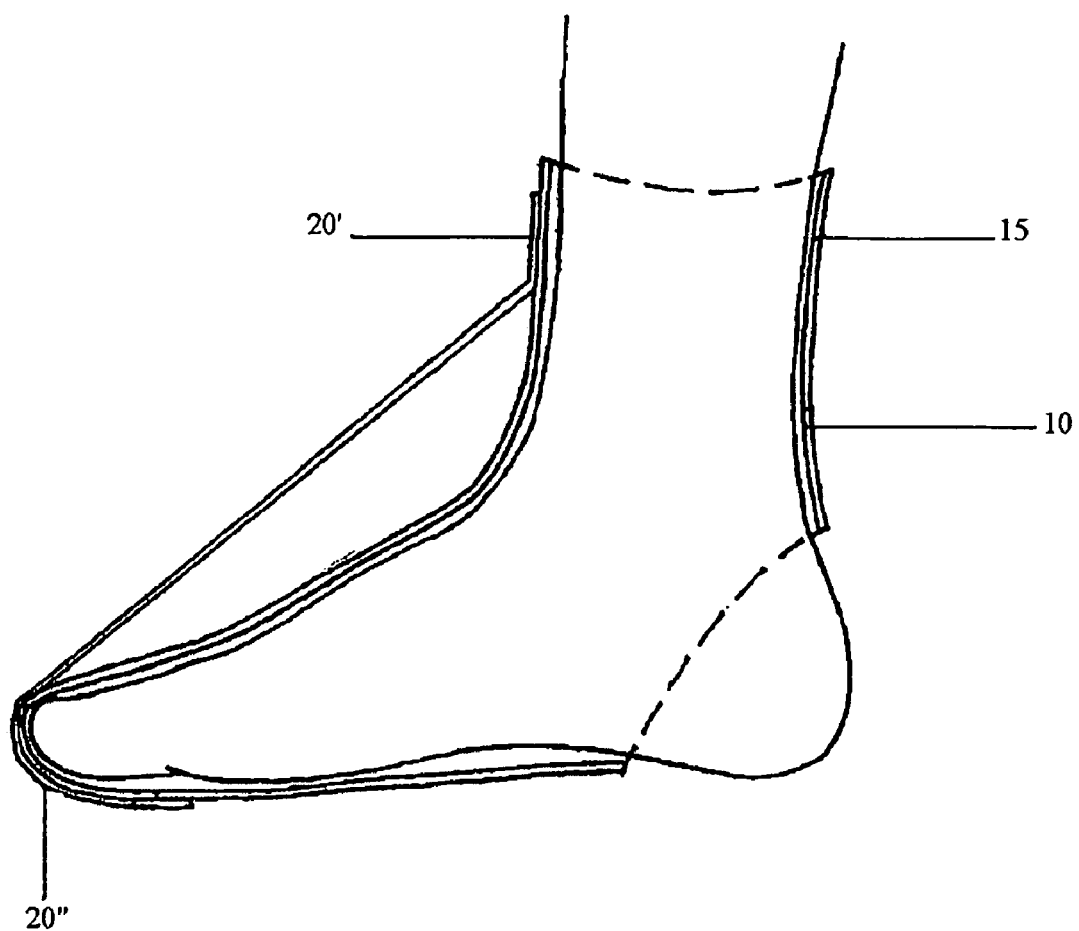
FIG. 5 shows a cross sectional view of a further device according to the present invention.

FIG. 5 shows a plan view of a further embodiment of the device of the present invention. In this embodiment the device is the same as that shown in FIG. 3 except that the leg binding (15) is integral with, and forms a portion of the elastic sock (10).

Figure 6:
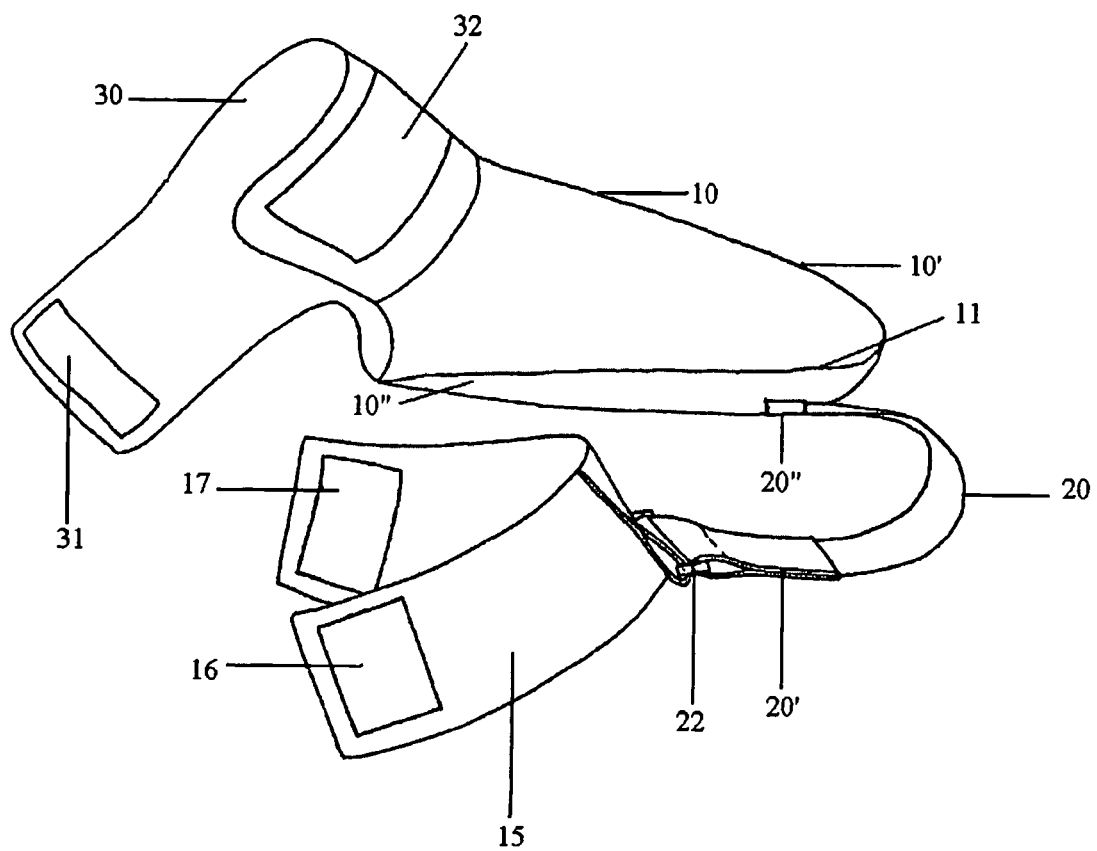
FIG. 6 shows a perspective view of the device of FIG. 1a when removed from the foot of the wearer.

FIG. 6 shows the device of FIG. 1 removed from the foot of the wearer. The elastic sock (10) is comprised of flexible rubberized material lined with absorbent cloth and comprises an upper portion (10') and a lower portion (10") held together by several lines of stitching (11). The elastic sock (10) encloses the foot (including the phalanges, metatarsals and area intermediate the metatarsals and the talus) and the ankle (including the lower part of the tibia and fibula). The binding is shaped such that in use the calcaneus (heel bone) of a wearer would be left exposed. The part of the elastic sock that encircles the ankle comprises a strip (30) that includes a patch of micro hooks (31) at its free end that in use can be removably attached to a patch of micro loops (32) located on the outer surface of the front of the elastic sock. The fit of the elastic sock can thus be adjusted by appropriately fitting together the two Velcro™ patches (31 and 32).

In this embodiment the leg binding (15) is a strip of elastic material that includes micro hooks (16) on the outer surface of one of its free ends and micro loops (17) on the inner surface of the other free end.

The elastic strap (20) has one end (20") integral with the lower portion (10") of the elastic sock (10), held in place by stitching. The other end (20') is threaded through a plastic loop (22) anchored to the front of the leg binding (15). The end (20') of the elastic strap (20) comprises micro hooks and micro loops and is thus fastened to itself. This end (20') can be used to adjust the length of the elastic strap between the elastic sock (10) and the leg binding (15).

The word 'comprising' and forms of the word 'comprising' as used in this description does not limit the invention claimed to exclude any variants or additions.

Modifications and improvements to the invention will be readily apparent to those skilled in the art. Such modifications and improvements are intended to be within the scope of this invention.

The claims defining the invention are as follows:

1. A device for a subject having plantar fasciitis, the device comprising:
   (a) an elastic sock, said sock comprising a toe portion having a distal end adapted to enclose a plurality of toes of the subject when in use;
   (b) a leg binding; and
   (c) an elastic strap, the elastic strap extending around a front portion of the toe portion or being connected to an upper surface of the toe portion, the elastic strap connecting the toe portion of the elastic sock to the leg binding,
   wherein the device is adapted to be used while the subject is walking and is configured to restrain the plantar fascia from flexion and permit the subject to exercise the plantar fascia while the subject is walking.

2. The device according to claim 1, wherein, when in use, the device is configured to resist contraction of the plantar fascia when the subject is at rest.

3. The device according to claim 1, wherein, when in use, the device is configured to keep the plantar fascia in a neutral to slight dorsiflexion by passive static tension, yet is configured to allow movement of the foot relative to the calf and ankle.

4. The device according to claim 1, wherein the elastic sock comprises an ankle portion configured to extend over the ankle of the wearer and enclose at least part of the subject's tibia and fibula.

5. The device according claim 1, wherein the elastic sock includes one or more openings.

6. The device according to claim 1, wherein the elastic sock further includes straps or tapes for adjusting the fit of the elastic sock to the subject's foot.

7. The device according to claim 1, wherein the elastic sock has an upper surface and a lower surface, which surfaces are integral.

8. The device according to claim 7, wherein the lower surface of the elastic sock includes a non-slip material.

9. The device according to claim 1, wherein the leg binding is integral with the elastic sock.

10. The device according to claim 1, wherein one end of the elastic strap is integral with the elastic sock.

11. The device according to claim 1, wherein, when in use, the leg binding is configured to be located adjacent the subject's ankle.

12. The device according to claim 1, wherein, when in uses the leg binding is configured to be located intermediate the ankle and knee of the subject.

13. The device according to claim 1, wherein the leg binding is configured to be wrapped around the calf or ankle of the wearer, and held closed by a hook and loop material fastening.

14. The device according to claim 1, wherein one end of the elastic strap is located adjacent the leg binding and is adjustable so the overall length of the elastic strap can be modified in order to maintain static tension on the plantar fascia.

15. The device according to claim 1, wherein the elastic sock is entirely made of flexible material.

16. The device according to claim 15, wherein the flexible material is a polymeric material or a combination of polymeric materials.

17. The device according to claim 16, wherein the flexible material is chosen from a group comprising neoprene, flexible rubberized material, polypropylene or polyurethane.

18. The device according to claim 15, wherein the flexible material has thermotherapeutic properties.

19. The device according to claim 1, wherein the leg binding is entirely made of flexible material.

20. The device according to claim 19, wherein the flexible material is a polymeric material or a combination of polymeric materials.

21. The device according to claim 20, wherein the flexible material is chosen from a group comprising neoprene, flexible rubberized material, polypropylene or polyurethane.

22. The device according to claim 19, wherein the flexible material has thermotherapeutic properties.

23. The device according to claim 1, wherein the elastic strap is entirely made of flexible material.

24. The device according to claim 23, wherein the flexible material is a polymeric material or a combination of polymeric materials.

25. The device according to claim 24, wherein the flexible material is chosen from a group comprising neoprene, flexible rubberized material, polypropylene or polyurethane.

26. The device according to any one of the preceding claims which stimulates blood flow to the subject's calf and foot.

27. The device according to claim 23, wherein the flexible material has thermotherapeutic properties.

28. The device according to claim 1, wherein the elastic strap is connected to a lower surface of the toe portion.

29. The device according to claim 1, wherein the elastic strap is connected to an upper surface of the toe portion.

30. The device according to claim 1, wherein the elastic strap comprises elastic material along its entire length.

31. The device according to claim 1, wherein the elastic strap comprises elastic material along part of its length.

* * * * *